(12) United States Patent
Beck

(10) Patent No.: US 9,265,435 B2
(45) Date of Patent: Feb. 23, 2016

(54) MULTI-ELECTRODE SENSING PATCH FOR LONG-TERM PHYSIOLOGICAL MONITORING WITH SWAPPABLE ELECTRONICS, RADIO AND BATTERY, AND METHODS OF USE

(75) Inventor: James C. Beck, Berkeley, CA (US)

(73) Assignee: HMICRO, INC., Fremont, CA (US)

( * ) Notice: Subject to any disclaimer, the term of this patent is extended or adjusted under 35 U.S.C. 154(b) by 470 days.

(21) Appl. No.: 12/739,553

(22) PCT Filed: Oct. 21, 2008

(86) PCT No.: PCT/US2008/080659
§ 371 (c)(1),
(2), (4) Date: Oct. 18, 2010

(87) PCT Pub. No.: WO2009/055397
PCT Pub. Date: Apr. 30, 2009

(65) Prior Publication Data
US 2011/0028822 A1    Feb. 3, 2011

Related U.S. Application Data

(60) Provisional application No. 60/982,233, filed on Oct. 24, 2007.

(51) Int. Cl.
*A61B 5/04* (2006.01)
*A61B 5/0408* (2006.01)
(Continued)

(52) U.S. Cl.
CPC ............ *A61B 5/0408* (2013.01); *A61B 5/0478* (2013.01); *A61B 5/0492* (2013.01); *A61B 2562/227* (2013.01)

(58) Field of Classification Search
CPC ............ A61B 5/0006; A61B 5/04085; A61B 5/6831; A61B 5/0408; A61B 5/0402; A61B 5/6804; A61B 2560/0468; A61B 5/02438; A61B 5/04; A61B 2560/0431; A61B 2560/0462; A61B 2560/0406; A61B 2560/0412; A61B 2562/16

USPC .......... 439/345–347, 909; 600/372, 382, 384, 600/386, 392–393, 508–509; 607/46, 48, 607/50, 72, 115
See application file for complete search history.

(56) References Cited

U.S. PATENT DOCUMENTS 3,786,391 A   1/1974   Mathauser
3,808,577 A   4/1974   Mathauser
(Continued)

FOREIGN PATENT DOCUMENTS

WO   WO 01/78594 A1   10/2001
WO   WO 02/089667 A1   11/2002
(Continued)

OTHER PUBLICATIONS

International search report and written opinion dated May 28, 2009 for PCT Application No. US08/80695.
(Continued)

*Primary Examiner* — Joseph Stoklosa
*Assistant Examiner* — Brian M Antiskay
(74) *Attorney, Agent, or Firm* — Wilson Sonsini Goodrich & Rosati

(57) ABSTRACT

Provided herein is an electrode device comprising an interface comprising at least one magnetic contact. The interface can be adaptable to be in communication with an electronic member, wherein the magnetic contact on the interface is adaptable to align and position the electronic member with respect to the interface. The interface can be further adaptable to remain affixed to a patient while an electronic member is removed and/or inserted from the interface. Further provided herein are methods of using the electrode device and kits.

41 Claims, 6 Drawing Sheets

(51) Int. Cl.
*A61B 5/0478* (2006.01)
*A61B 5/0492* (2006.01)

(56) References Cited

U.S. PATENT DOCUMENTS

| | | | |
|---|---|---|---|
| 4,067,342 | A | 1/1978 | Burton |
| 4,082,086 | A | 4/1978 | Page et al. |
| 4,084,583 | A | 4/1978 | Hjort |
| 4,121,573 | A | 10/1978 | Crovella et al. |
| 4,365,634 | A | 12/1982 | Bare et al. |
| 4,398,545 | A * | 8/1983 | Wilson .................. 607/152 |
| 4,653,503 | A | 3/1987 | Heath |
| 5,372,125 | A | 12/1994 | Lyons |
| 5,578,065 | A * | 11/1996 | Hattori et al. .................. 607/46 |
| 5,895,369 | A | 4/1999 | Flower |
| 6,104,306 | A | 8/2000 | Hogue et al. |
| 6,441,747 | B1 | 8/2002 | Khair et al. |
| 6,456,720 | B1 | 9/2002 | Brimhall et al. |
| 6,897,788 | B2 | 5/2005 | Khair et al. |
| 6,965,794 | B2 | 11/2005 | Brody |
| 7,156,301 | B1 | 1/2007 | Bonalle et al. |
| 7,257,438 | B2 * | 8/2007 | Kinast .................. 600/509 |
| 7,400,298 | B2 | 7/2008 | Fogg et al. |
| 7,668,580 | B2 | 2/2010 | Shin et al. |
| 7,796,042 | B2 | 9/2010 | Walther et al. |
| 7,920,096 | B2 | 4/2011 | Fogg et al. |
| 7,969,307 | B2 | 6/2011 | Peeters |
| 7,970,450 | B2 | 6/2011 | Kroecker et al. |
| 8,287,386 | B2 | 10/2012 | Miller et al. |
| 8,628,020 | B2 | 1/2014 | Beck et al. |
| 8,718,742 | B2 | 5/2014 | Beck et al. |
| 2003/0040305 | A1 | 2/2003 | Ng et al. |
| 2006/0009691 | A1 | 1/2006 | Yeo et al. |
| 2006/0155183 | A1 | 7/2006 | Kroecker et al. |
| 2006/0264767 | A1 | 11/2006 | Shennib |
| 2007/0060832 | A1 | 3/2007 | Levin |
| 2007/0072443 | A1 | 3/2007 | Rohrbach et al. |
| 2007/0093705 | A1 * | 4/2007 | Shin et al. .................. 600/372 |
| 2007/0179376 | A1 | 8/2007 | Gerder |
| 2008/0055045 | A1 | 3/2008 | Swan et al. |
| 2008/0309287 | A1 | 12/2008 | Reed |
| 2009/0036792 | A1 | 2/2009 | DeLuca et al. |
| 2010/0317958 | A1 | 12/2010 | Beck et al. |
| 2010/0326703 | A1 | 12/2010 | Gilad et al. |
| 2011/0062241 | A1 | 3/2011 | Beck |
| 2011/0065476 | A1 | 3/2011 | Hsiao et al. |
| 2011/0299713 | A1 | 12/2011 | Moller et al. |
| 2015/0073231 | A1 | 3/2015 | Beck et al. |

FOREIGN PATENT DOCUMENTS

| | | |
|---|---|---|
| WO | WO 03/065926 A2 | 8/2003 |
| WO | WO 03/065926 A3 | 6/2004 |
| WO | WO 2005/094674 A1 | 10/2005 |
| WO | WO 2006/061354 A1 | 6/2006 |
| WO | WO 2007/060609 A2 | 5/2007 |
| WO | WO 2007/060609 A3 | 10/2007 |
| WO | WO 2008/006150 A1 | 1/2008 |

OTHER PUBLICATIONS

International search report and written opinion dated Jul. 20, 2009 for PCT Application No. US08/80659.
International search report and written opinion dated Sep. 29, 2008 for PCT Application No. US08/64800.
Office action dated Apr. 15, 2013 for U.S. Appl. No. 12/601,373.
Office action dated Jun. 26, 2012 for U.S. Appl. No. 12/739,561.
Office action dated Aug. 31, 2012 for U.S. Appl. No. 12/601,373.
U.S. Appl. No. 14/244,760, filed Apr. 13, 2014, Beck et al.
Notice of allowance dated Mar. 14, 2014 for U.S. Appl. No. 12/601,373.
Notice of allowance dated Sep. 12, 2013 for U.S. Appl. No. 12/739,561.
Office action dated Oct. 29, 2013 for U.S. Appl. No. 12/601,373.
U.S. Appl. No. 14/091,252, filed Nov. 26, 2013, Beck.
Office action dated Jan. 22, 2015 for U.S. Appl. No. 14/091,252.
Office action dated Feb. 27, 2015 for U.S. Appl. No. 14/244,760.
Co-pending U.S. Appl. No. 14/805,389, filed Jul. 21, 2015.

* cited by examiner

MULTI-ELECTRODE SENSING PATCH FOR LONG-TERM PHYSIOLOGICAL MONITORING WITH SWAPPABLE ELECTRONICS, RADIO AND BATTERY, AND METHODS OF USE

CROSS-REFERENCE

This application claims the benefit of U.S. Provisional Application No. 60/982,233, filed Oct. 24, 2007, which application is incorporated herein by reference in its entirety.

BACKGROUND OF THE INVENTION

When long-term monitoring—from a few hours to multiple months—of human-generated signals (such as electrocardiogram (ECG), electroencephalogram (EEG) and electromyogram (EMG)) is required, currently available devices fall short of adequately meeting the requirements of both the clinician and patient. A medical patch is typically a thin, adhesive-coated flexible material applied to the skin, in this case, for medical monitoring or therapy (drug, electric stimulus, etc.) delivery. A patch may additionally be comprised of one part attached to the skin and a second part that includes electronics circuitry, a radio and a battery, which is in turn attached to the first (skin) part. For long-term monitoring applications, it may be important to leave the skin-contacting portion of the patch attached for the entire monitoring period. Not only will this yield the most consistent signals, but the patient's skin will experience less trauma resulting from the patch. Adhesives commonly used for attaching ambulatory electrodes or patches typically remove one or two layers of skin when they are pulled off, and repeated removals at the same body site can cause skin trauma and a painful rash. Reapplying a patch to a different site avoids the skin irritation, but is unlikely to produce identical signals in monitoring applications.

To accommodate leaving the electrodes in place for extended periods, a method for removing and replacing the electronics, radio and battery is needed. Replaceability of the electrodes/electronics is desirable for the following reasons including: replacing batteries, preventing damage to the electronics during swimming or bathing, replacing malfunctioning electronics, radios or battery, reducing discomfort during certain physical activities, eliminating interference while undergoing medical scanning procedures, and/or removing a battery or capacitor power supply for recharging.

It would be desirable to develop a wireless patch for long-term monitoring, including the ability to change out or swap the electronics circuitry, radio and battery, either as a single unit or in separate modules, without having to remove the electrodes contacting the patient's skin.

SUMMARY OF THE INVENTION

Provided herein is an electrode device comprising an interface. The interface comprises at least one magnetic contact, the interface adaptable to be in communication with an electronic member. The magnetic contact can be adaptable to slidably align and position the electronic member with respect to the interface. The interface can be further adaptable to remain affixed to a patient while the electronic member used with the interface can be removed and/or inserted from the interface. The interface can be a pouch, pocket or container. Additionally, the device can further comprise an electronic member. In some embodiments, the device can be a flexible substrate. The magnetic contact on the interface can be used with the electronic device to align and position the electronic member. Alternatively, the magnetic contact on the interface can be used with a contact on the electronic member to align and position the electronic member with respect to the electronic interface. The electronic member can be a replaceable electronic member such that the electronic member can be removed from the interface and reinserted into the interface without disturbing the interface. Alternatively, the electronic member can be removed from the interface and replaced with another electronic interface without disturbing the interface. Multiple electronic members can be used with the electronic interface. In some embodiments, the electrode device can further comprise a ferromagnetic metal adaptable to facilitate the connection between the interface and the electronic member. The ferromagnetic metal can be located on the interface and form a connection with a magnet that is part of the electronic member. Alternatively, the ferromagnetic metal can be located on the electronic member and form a connection with a magnet that is part of the interface. In addition to forming a connection between the interface and the electronic member, the interface can also maintain the connection between the electronics member and the interface. The contact on the interface can be used to maintain the connection between the electronics member and the interface. In some embodiments, an additional support structure can be used with the interface to maintain the connection between the interface and the electronics member. The additional support can be a tab holding the electronic member in communication with the interface. The additional support can be a slot that can be used to hold the electronic member in communication with the interface. The magnetic contact can be adaptable to provide a low engagement force between the interface and the electronic member.

Further provided herein is an electrode device comprising an interface in communication with a patient, an electronic member adaptable to be inserted and/or removed from the interface without disturbing the interface, and at least one compliant electronic connection. The interface can be adaptable to slidably engage the electronic member. The interface can facilitate self-alignment and self-positioning of the electronic member in the interface. The interface can be a pouch, pocket or container. In some embodiments, the interface can be a flexible substrate. In some embodiments, the electrode device can comprise more than one compliant electronic connection. The device can further comprise an interface that has at least one contact located on the interface. The contact can be adaptable to facilitate the self-alignment and self-positioning of the electronic member with respect to the interface. Furthermore, the electronic member can be adaptable to be inserted, removed, and then reinserted into the interface. Alternatively, the electronic member can be inserted, removed, and replaced with a second electronic member. In some embodiments, the interface can be adaptable to be in communication with more than one electronic component. The interface can be in communication with more than one electronic component at the same time. In some cases, the interface can be in communication with more than one electronic component having different configurations.

Further provided here in is a method for detecting a physiological parameter with at least one electrode comprising: positioning an interface on the surface of a patient; sliding an electronic member into contact with the interface to engage the electronic member with the interface; and detecting the physiological parameter from the patient. The electronics member can be adaptable to be inserted and/or removed from the interface without disturbing the interface. The method can further comprise the step of removing the electronic member from the interface and replacing the electronic member with a second electronic member. The second electronic member can be the same electronic member as the first electronic member. Alternatively, the second electronic member can be a different electronic member than the first electronic member. The method can further comprise the use of an interface wherein the interface comprises at least one magnetic contact, the interface adaptable to be in communication with an electronic member, wherein the at least one magnetic contact is adaptable to align and position the electronic member in the interface. The interface can be a pouch, pocket or container. The method can comprise a device that can be designed such that the device can be adaptable to facilitate insertion of the electronic member in the interface. The device can slidably engage the communication member with the interface.

Further provided herein is a method of detecting a physiological parameter comprising: forming an interface from a flexible substrate, the flexible substrate comprising at least one magnetic contact; sliding the interface in contact with a surface of a patient; inserting an electronic member in the interface, the electronic member comprising at least one magnetic contact; connecting the interface and electronic member using the at least one magnetic contact on the interface and the at least one contact on the electronic member; and detecting at least one physiological parameter from the patient. The interface can be further adaptable to remain affixed to a patient while the electronic member is removed and/or inserted with respect to the interface. Additionally, the method can provide the step of disconnecting the electronic member from the interface and reconnecting an electronic member with the interface. The electronic member reconnected with the interface can be the original electronic member. Alternately, the electronic member reconnected with the interface can be a new electronic member.

Provided herein is a method for detecting a physiological parameter from a patient comprising: sliding an electronic member into contact with an interface adaptable to be in communication with the electronic member; and positioning the interface on a surface of a patient. The interface can be further adaptable to remain affixed to a patient while the electronic member is removed and/or inserted with respect to the interface. Additionally, the method can further comprise the step of removing the electronic member and reinserting the electronic member. Alternatively, the method can further comprise the step of removing the electronic member and replacing the electronic member with a second electronic member.

Further provided herein is a kit for measuring a physiological parameter comprising: an interface comprising at least one magnetic contact, the interface adaptable to be in communication with an electronic member, the at least one magnetic contact adaptable to slidably engage the electronics member and if further adaptable to align and position the electronic member with respect to the interface. The kit can further comprise an electronic member.

Provided herein is a kit for measuring a physiological parameter comprising: an interface having at least one magnetic contact, the interface adaptable to be in communication with an electronic member; and at least one electronic member, the at least one magnetic contact adaptable to slidably align and position the electronic member with respect to the interface. The kit can further comprise more than one electronic member.

INCORPORATION BY REFERENCE

All publications, patents, and patent applications mentioned in this specification are herein incorporated by reference to the same extent as if each individual publication, patent, or patent application was specifically and individually indicated to be incorporated by reference in their entirety.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
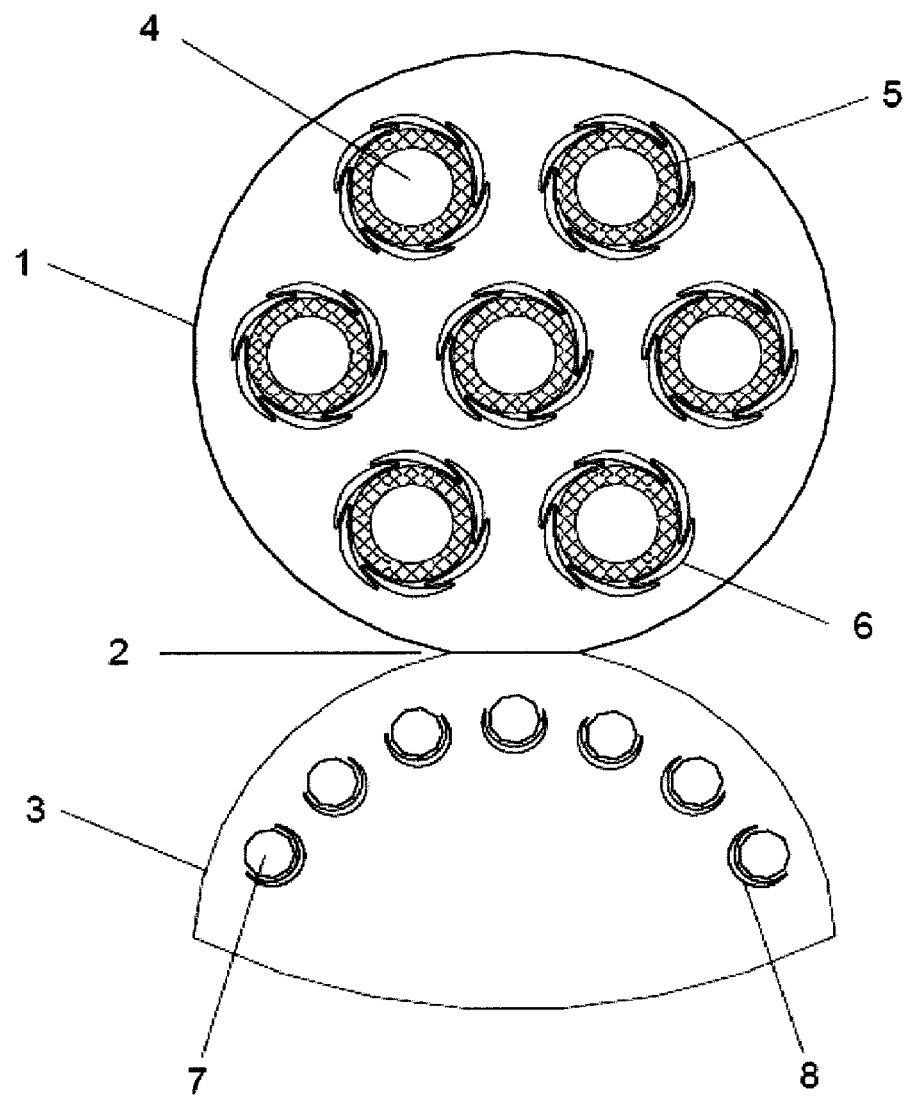
FIG. 1 illustrates an outer view of one embodiments of an unfolded patch.

The invention described herein includes is a device that uses replaceable (swappable) components. Provided herein is a device that can be adhered to the surface of a patient. The device can be placed at the beginning of the monitoring period and remain in place until sufficient data has been collected. The device can comprise several electrode connections that are in communication with the skin of the patient. The electrodes can be adaptable to collect multiple views of the desired human generated signal. The ability of a patch to collect multiple views has been described previously in U.S. Provisional Application Ser. No. 60/940,072 entitled "An Integrated Wireless Patch for Physiological Monitoring."

Further provided herein is a system with a replaceable electronics device comprising an interface adaptable to be adhered to the patient, a circuit board or electronics member comprising at least one radio and at least one battery subsystem, the circuit board being adaptable to be connected to the interface. The circuit board can perform various functions including, but not limited to, detection, amplification, processing, storage, transmittal, or any combination thereof. The method for mechanically and electrically connecting the electrodes to the electronics subsystem has some unique requirements. The method of connecting the electronics together includes making it easier for patients with limited manual dexterity to insert and remove the electronics module. The low insertion and extraction forces of the device and self-alignment further aids patient use. The design of the device also makes for a reliable and robust electrical connection especially during patient movement and during connection/disconnection cycles.

Provided herein is an electrode device comprising an interface. The interface comprises at least one magnetic contact, the interface adaptable to be in communication with an electronic member. The magnetic contact can be adaptable to slidably align and position the electronic member with respect to the interface. The interface can be further adaptable to remain affixed to a patient while the electronic member used with the interface can be removed and/or inserted from the interface. The interface can be a pouch, pocket or container. Additionally, the device can further comprise an electronic member. In some embodiments, the device can be a flexible substrate. The magnetic contact on the interface can be used with the electronic device to align and position the electronic member. Alternatively, the magnetic contact on the interface can be used with a contact on the electronic member to align and position the electronic member with respect to the electronic interface. The electronic member can be a replaceable electronic member such that the electronic member can be removed from the interface and reinserted into the interface without disturbing the interface. Alternatively, the electronic member can be removed from the interface and replaced with another electronic interface without disturbing the interface. Multiple electronic members can be used with the electronic interface. In some embodiments, the electrode device can further comprise a ferromagnetic metal adaptable to facilitate the connection between the interface and the electronic member. The ferromagnetic metal can be located on the interface and form a connection with a magnet that is part of the electronic member. Alternatively, the ferromagnetic metal can be located on the electronic member and form a connection with a magnet that is part of the interface. In addition to forming a connection between the interface and the electronic member, the interface can also maintain the connection between the electronics member and the interface. The contact on the interface can be used to maintain the connection between the electronics member and the interface. In some embodiments, an additional support structure can be used with the interface to maintain the connection between the interface and the electronics member. The additional support can be a tab holding the electronic member in communication with the interface. The additional support can be a slot that can be used to hold the electronic member in communication with the interface. The magnetic contact can be adaptable to provide a low engagement force between the interface and the electronic member.

Further provided herein is an electrode device comprising an interface in communication with a patient, an electronic member adaptable to be inserted and/or removed from the interface without disturbing the interface, and at least one compliant electronic connection. The interface can be adaptable to slidably engage the electronic member. The interface can facilitate self-alignment and self-positioning of the electronic member in the interface. The interface can be a pouch, pocket or container. In some embodiments, the interface can be a flexible substrate. In some embodiments, the electrode device can comprise more than one compliant electronic connection. The device can further comprise an interface that has at least one contact located on the interface. The contact can be adaptable to facilitate the self-alignment and self-positioning of the electronic member with respect to the interface. Furthermore, the electronic member can be adaptable to be inserted, removed, and then reinserted into the interface. Alternatively, the electronic member can be inserted, removed, and replaced with a second electronic member. In some embodiments, the interface can be adaptable to be in communication with more than one electronic component. The interface can be in communication with more than one electronic component at the same time. In some cases, the interface can be in communication with more than one electronic component having different configurations.

I. Devices

The devices described herein is a patch comprising a thin, flexible material of suitable size and shape adaptable to collect physiological signals with multiple electrode contacts and adhesives on one side. In some embodiments, the device shape comprises a circle. The circle can have a diameter of approximately 50 mm. In some embodiments, the device shape comprises a square. The device shape can comprise any suitable shape. In some embodiments, the distance across the longest axis of the device can be approximate 20 mm. In some embodiments, the distance across the longest axis of the device can be approximately 10 mm. In some embodiments, the distance across the longest axis of the device can be approximately 100 mm.

On the back side of the device, a second piece of flexible material in approximately the same shape as the first piece. The second piece of material joins with the first piece of material to form a interface. The second piece of material can be a separate piece of material from the first piece of material. Alternatively, the second piece of material can be the same piece of material as the first piece of material, where the second piece of material is comprised of a folded over portion of the first piece of material, as seen in FIG. 1. FIG. 1 is an outside view of one embodiment of a device, where the first and second pieces of material can form a interface and that are part of the same piece of material. In the embodiment shown in FIG. 1 the device is unfolded. The first piece of material 1 is connected to the second piece of material 3 at the fold line 2. The second piece 3 is folded into contact with the first piece of material 1 at the hinge 2. The first and second substrates can then be joined together along the edges to form an interface.

Materials from which the interface can be made include biodegradable materials and biocompatible materials. In some embodiments, the interface can be made from a "plastic" sheet material, where the plastic material has suitable mechanical and electrical characteristics. Alternatively, the interface can be fabricated from a woven material for increased flexibility.

FIG. 1 also illustrates the first substrate 1 comprising electrodes contact areas 4 that can come into contact with the patient's skin. The number of electrodes on the substrate can be adjusted based on the application for which the device is needed. Additionally, the electrode configuration can also be varied depending on the application.

The second piece of material 3 when folded upward along the hinge 2 and sealed together with the first piece of material 1 forms the interface. The second piece of material 3 can be folded away from the patient. In some embodiments, the second piece of material 3 is substantially the same shape as the first piece of material 1. In some embodiments, the second piece of material is only a portion of the size of the first piece of material 1. In some embodiments, the second material is at least half of the size of the first material. The electronic member that is inserted into the interface may extend from the interface.

The outside of the first piece of substrate 1 as shown FIG. 1 can be positioned in contact with the patient. The outer surface of the first piece of substrate can have gel contact areas 4 that are in communication with the patient and in communication with the external electronics. The external electronics include the electronic module, or any other suitable external electronic component. In some embodiments, once the second piece of material is attached to the first piece of material, circular donut pads can be cut around the gel contact areas 4 to expose an adhesive section 5. The adhesive 5 can be a biocompatible adhesive that can facilitate sticking the device to the patient's skin. After the adhesive section 5 is formed, a gel can be positioned on the electrode gel contact areas. The gel can be in contact with conducting rivets located through the substrate carry any physiological signal detected to the inside of the interface. The metallic rivets and conducting traces may be fabricated from carbon based or other conductive materials without loss of function. These materials may be more compatible with magnetic resonance (MR) imaging, allowing the patch to remain in place during the procedure, while the electronics module is removed.

The second piece of material 3 can further comprise ferromagnetic disks 7. The ferromagnetic disks 7 can be used to form a connection between the device and an electronics board. In some embodiments, the connection is an electrical connection. In some embodiments, the connection is a mechanical connection. The connection can be both a mechanical and an electrical connection. The disks 7 can be attracted to magnets located on the electronics board. In some embodiments, crescent shaped cut-outs 8 are located around each ferromagnetic disk. The cut-outs allow the disks to independently comply with slight mechanical differences. The cut-outs can also facilitate the use of smaller magnets and ferromagnetic disks. The ferromagnetic disks, on the other hand, may not be compatible with MR procedures, and may require removal. By definition, they need to respond to a magnetic field in order to provide the connection function described in this patent, and the large magnetic fields employed in MR imaging could cause them to overheat or interfere with the imaging process.

Since the disks do not provide an electric connection per se, it is possible to remove them for an MR procedure and then replace them afterwards. A single adhesive carrier strip would contain the disks for easy removal and replacement. Such a design would also have benefits for recycling, as the disks could be easily removed and discarded, or recycled separately before recycling the interface.

Figure 2:
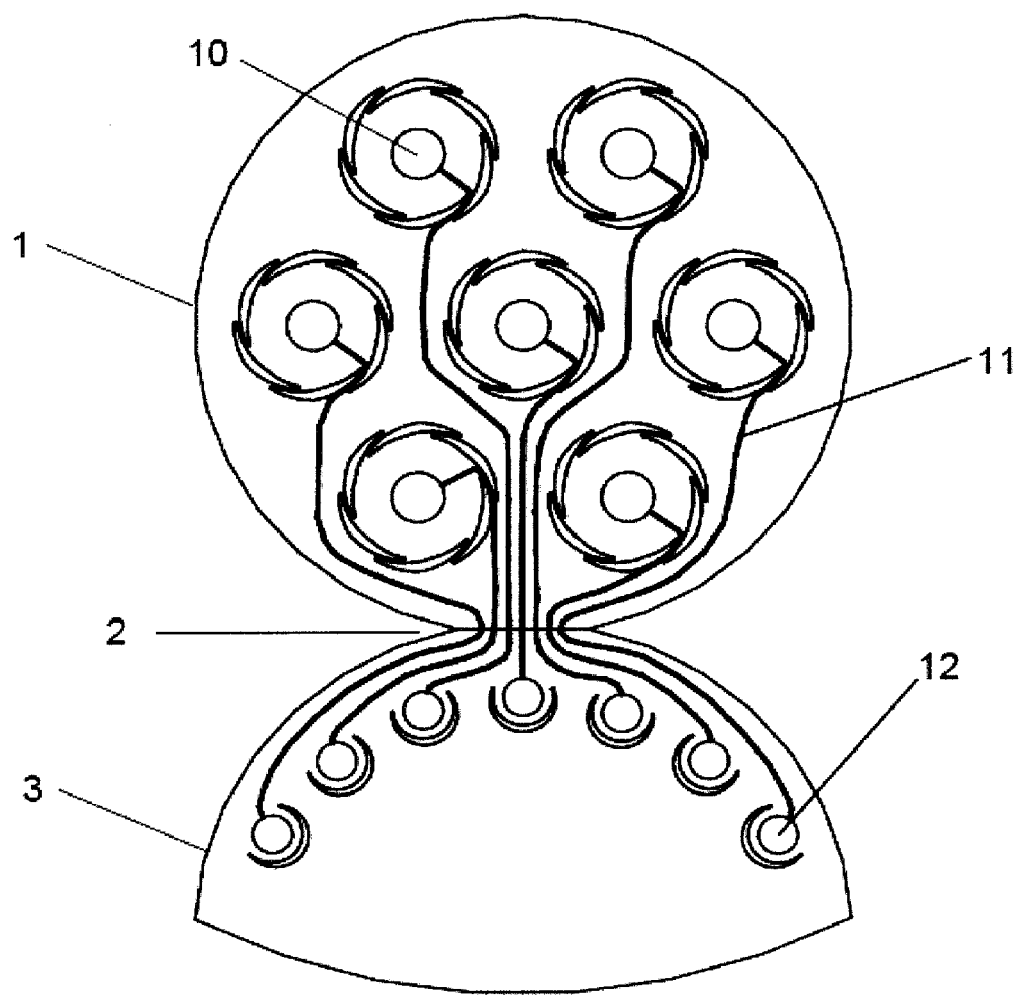
FIG. 2 illustrates an inner view of one embodiment of an unfolded patch.

FIG. 2 illustrates the inside of the device showing the second piece of material 3 unfolded from the first piece of material 1. FIG. 2 illustrates the interior of the electrode contact areas as seen in FIG. 1. FIG. 2 illustrates the contacts 10 that are in communication with the patient's skin surface through the gel as shown in FIG. 1. The contacts can be made from metal, carbon, composite materials, or any suitable combination thereof. Once the signal has reached the contact 10 on the inside of the interface, the signal can be carried to a second set of contact patches 12 located on the second piece of material. The contacts 10 located on the first piece of material and the contact patches 12 located on the second piece of material are in communication with each other. In some embodiments, the contacts 10 and the contact patches 12 are in communication with each other through traces 11. The traces 11 can be conductive traces. The traces can be made out of gold, platinum, or any other suitable metal from which the traces can be formed. In some embodiments, the traces can be mad from any suitable non-metallic conductor. The contact patches 12 are located underneath the ferromagnetic disks 7 as shown in FIG. 1.

The contact patches make contact with the electronics with a circuit board. The contact patches can be plated with a conductive material. The contact material choice and fabrication method can depend on specific application requirements. Additional treatments can be applied to the contact patches to improve the functionality of the contact area including, but not limited to, forming a dimple in the contact area. A series of spiral cut-outs 6 in the substrate material around each skin contact electrode can improve patient comfort by allowing some amount of independent electrode movement.

After the first and second parts of the substrate, 1 and 3, respectively, are folded together along the hinge 2, they can be joined together along the periphery to form a pouch, pocket or container. The first and second parts of the substrate can be joined together using any suitable joining method including, but not limited to, thermal bonding, using glue, or other suitable adhesives, or by additional external features that allow the two parts of the substrate to be snapped together, or any combination thereof. In some embodiments, the shape of the substrate can be altered to facilitate the bonding of the substrate parts. For example purposes only, tabs can be added to the substrate shape to define the bonding area. In some embodiments, the joining of the first and second part of the substrates is in the form of a tight seal. In some embodiments, the first and second parts of the substrates are joined together in a discontinuous manner. This can allow water to drain from the interface after swimming or bathing or other situations including water exposure.

Figure 3:
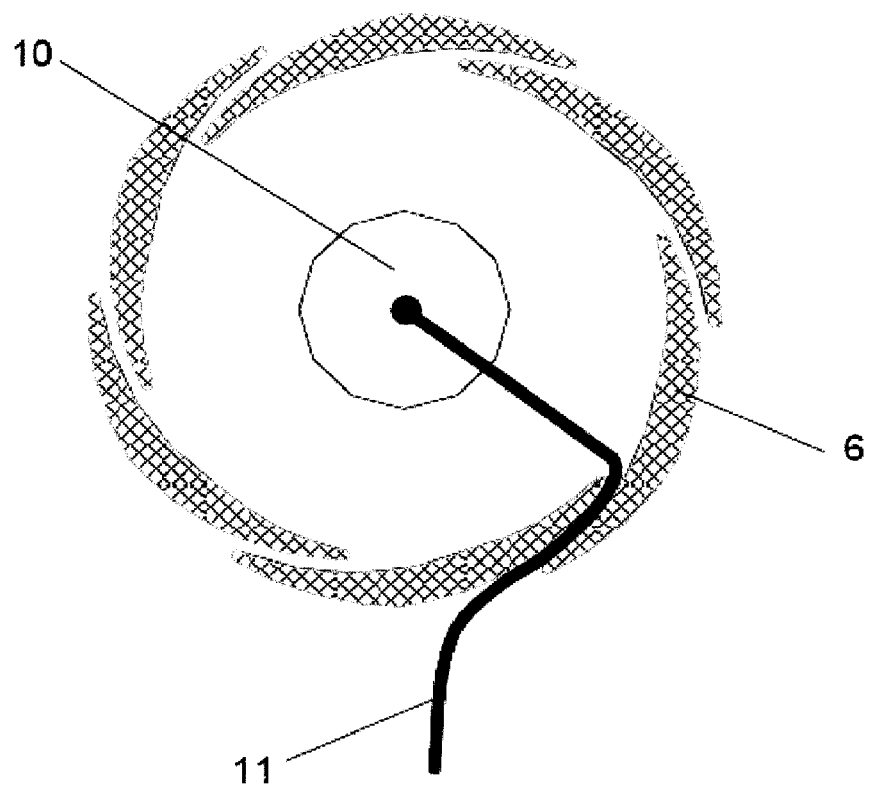
FIG. 3 illustrates an isolated view of one embodiment of an electrode contact from as viewed from the inner side of the substrate.

A close-up view of one embodiment of one of the electrode is shown in FIG. 3. FIG. 3 illustrates an electrode comprising a contact 10 and a trace 11 exiting from the contact 10. The electrode can be surrounded by spiral shaped cut-outs 6 to facilitate individual movement of the electrode to reduce the strain between the electrode and the surface of the patient. The spiral cutting 6 around the electrode can allow the contacts to float somewhat with respect to the substrate and/or with respect to each other. The spiral cut can be created by any suitable means including, cutting, burning, etching or punching the substrate material, or any combination thereof. The central contact 10 is then supported by bridges located in between the cut-outs. The trace exits the contact along one of the bridges. In some embodiments, only one trace exits from the contact, as shown in FIG. 3. In some embodiments, more than one trace exits from the contact. The spiral bridges allow for more flexibility than using radial bridges. In some embodiments, the spiral bridges can be embossed with a three dimensional pattern, such as corrugation, that can provide for even more flexibility, especially with regards to circumferential or turning motions. In some embodiments, spiral shaped bridges are used. In some embodiments, radial bridges can be used.

Figures 4A, 4B:
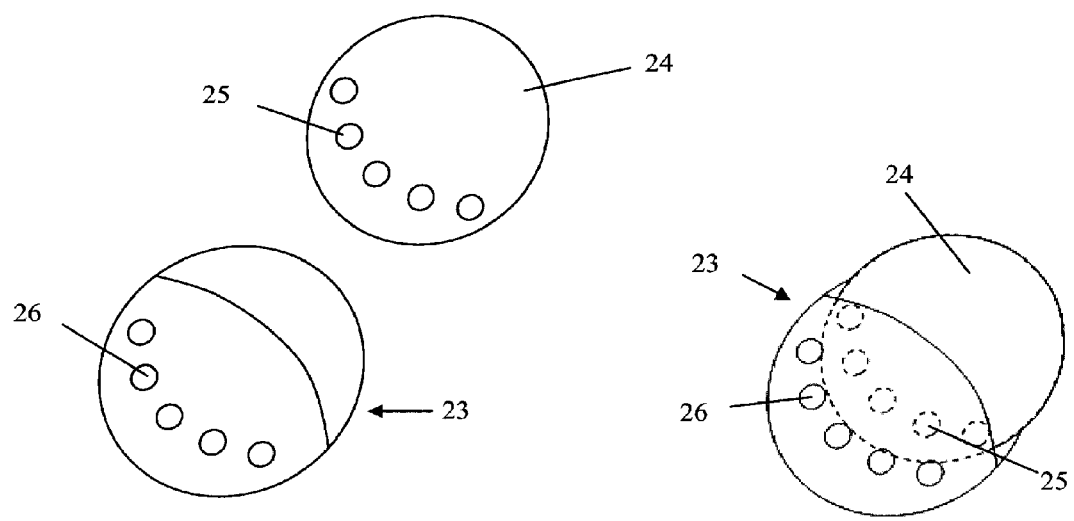
FIGS. 4A-4C illustrates steps for slidably engaging an electronics component with an interface.
Figure 4C:
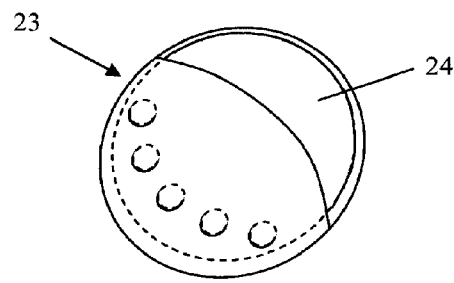

The electronics member 24, or circuit board, that can be used with the interface 23 as described herein, comprises a circuit board and a battery. The electronics member 24 can comprise an array of magnets 25 as shown in FIG. 4A. The array of magnets 25 can be positioned such that the magnets 25 correspond to the positions of the plated contact 26 of the interface 23. As shown in FIG. 4B, once the electronics member 24 is inserted into the interface 23, the magnets 25 will pull the ferromagnetic disks 26 toward the circuit board, thereby closing the circuits between the plated contacts and the circuit board, as shown in FIG. 4C. The position and force of the magnets can also be used to provide an alignment function and the electronics module is being inserted. Additionally, the connection formed between the interface and the electronics module can serve as mechanical restraints to hold the electronics module in place during use. The electronics member can be used to detect, amplify, process, store, and/or transmit signals.

Figure 5A:
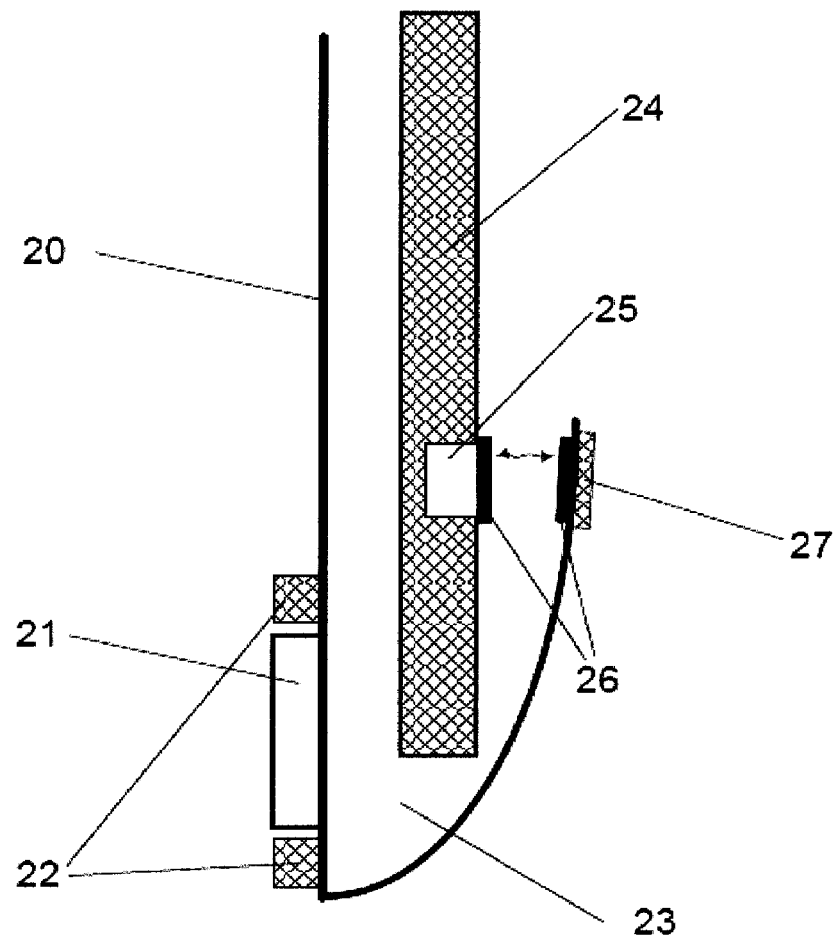
FIG. 5A is a side view of the interface being formed between the substrate and the circuit board.
Figure 5B:
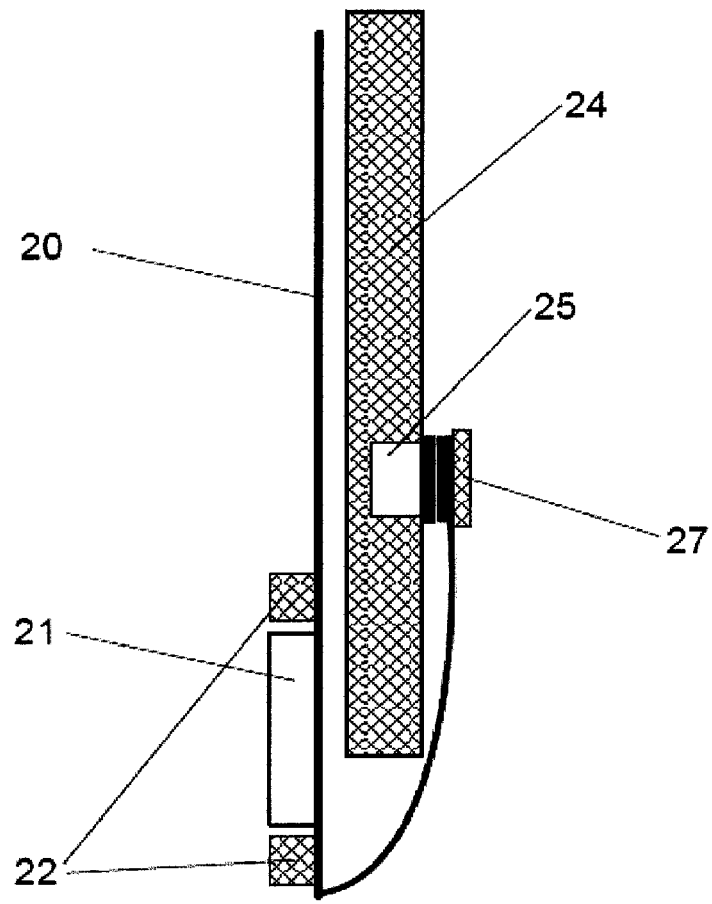
FIG. 5B is a side view of the interface with the electronics mated.

FIGS. 5A and 5B illustrate cut-away side views of the interface with electronics member. In FIG. 5A, the electronic module 24 has been inserted into the interface 23, but the connections between the electronics member 24 and the interface 23 have not been made. In some embodiments, magnets can be located along the surface of the electronics member. In embodiments, magnets 25 can be located in the interior of the circuit board 24, as shown in FIG. 5A. The ferromagnetic metal 27 can be positioned on the second part of the substrate 3 and the magnet 25 positioned near the electronics member. Alternatively, the ferromagnetic metal 27 can be positioned on the electronics member and the magnet positioned on the second part of the substrate. The magnet and ferromagnetic metal can then bring the contacts 26 on the electronic member and interface together. Alternate designs using one magnet to complete more than a single circuit are also possible. In addition, the polarity of the magnets can be used to align the electronics member in the interface. This is particularly true if one or more of the ferromagnetic metal disks are replaced with a magnet. The repulsion and attraction forces of the magnets could then help to guide the circuit board into proper position. FIG. 5A further illustrates the electrode gel 21 positioned in the adhesive 22 on the first part of the substrate.

FIG. 5B illustrates the electronic member 24 positioned in the interface. In FIG. 5B, the electronic member and the interface are mated together as indicated by the touching of the contact pads 26 on the interface 23 and electronic member 24.

Magnetic forces can be used to hold the electronics module in position in the interface. Additionally, other features can be used with the device to hold the electronic member in position. For example purposes only, the device can comprise a tab on the rear of the interface that can engage a portion of the electronics module. The tab can directly engage the electronics module. Alternatively, the tab can engage a slit located on the electronics module. Alternatively, the interface can comprise a slit which can engage the electronics module thereby holding it in place.

Described herein is a device comprising magnets for aligning an electronics board with respect to the interface. In some embodiments, the device can comprise alternative features for aligning and engaging the electronics board. Alternative features include any suitable feature that has a low insertion force engagement mechanism including a spring force to hold the electronics member in position including, but not limited to, clamps to hold the electronics member in position from behind, interfaces which can be clamped over the electronics member, or any other suitable method for engaging the electronics module, which allows for rapid and easy removal of the electronics member from the interface.

III. Methods

Further provided here in is a method for detecting a physiological parameter with at least one electrode comprising: positioning an interface on the surface of a patient; sliding an electronic member into contact with the interface to engage the electronic member with the interface; and detecting the physiological parameter from the patient. The electronics member can be adaptable to be inserted and/or removed from the interface without disturbing the interface. The method can further comprise the step of removing the electronic member from the interface and replacing the electronic member with a second electronic member. The second electronic member can be the same electronic member as the first electronic member. Alternatively, the second electronic member can be a different electronic member than the first electronic member. The method can further comprise the use of an interface wherein the interface comprises at least one magnetic contact, the interface adaptable to be in communication with an electronic member, wherein the at least one magnetic contact is adaptable to align and position the electronic member in the interface. The interface can be a pouch, pocket or container. The method can comprise a device that can be designed such that the device can be adaptable to facilitate insertion of the electronic member in the interface. The device can slidably engage the communication member with the interface.

Further provided herein is a method of detecting a physiological parameter comprising: forming an interface from a flexible substrate, the flexible substrate comprising at least one magnetic contact; sliding the interface in contact with a surface of a patient; inserting an electronic member in the interface, the electronic member comprising at least one magnetic contact; connecting the interface and electronic member using the at least one magnetic contact on the interface and the at least one contact on the electronic member; and detecting at least one physiological parameter from the patient. The interface can be further adaptable to remain affixed to a patient while the electronic member is removed and/or inserted with respect to the interface. Additionally, the method can provide the step of disconnecting the electronic member from the interface and reconnecting an electronic member with the interface. The electronic member reconnected with the interface can be the original electronic member. Alternately, the electronic member reconnected with the interface can be a new electronic member.

Provided herein is a method for detecting a physiological parameter from a patient comprising: sliding an electronic member into contact with an interface adaptable to be in communication with the electronic member; and positioning the interface on a surface of a patient. The interface can be further adaptable to remain affixed to a patient while the electronic member is removed and/or inserted with respect to the interface. Additionally, the method can further comprise the step of removing the electronic member and reinserting the electronic member. Alternatively, the method can further comprise the step of removing the electronic member and replacing the electronic member with a second electronic member.

IV. Kits

Further provided herein is a kit for measuring a physiological parameter comprising: an interface comprising at least one magnetic contact, the interface adaptable to be in communication with an electronic member, the at least one magnetic contact adaptable to slidably engage the electronics member and if further adaptable to align and position the electronic member with respect to the interface. The kit can further comprise an electronic member.

Provided herein is a kit for measuring a physiological parameter comprising: an interface having at least one magnetic contact, the interface adaptable to be in communication with an electronic member; and at least one electronic member, the at least one magnetic contact adaptable to slidably align and position the electronic member with respect to the interface. The kit can further comprise more than one electronic member.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An electrode device comprising:
   a pouch formed of a flexible substrate having a first part and a second part that are inseparably joined together along a periphery, the pouch having an interior and comprising at least one electrode contact area on a surface of the first part and at least one contact patch on an interior surface of the second part, the at least one electrode contact area connected to the at least one contact patch via a conductive trace traversing a distance along the flexible substrate over both the first part of the pouch and the second part of the pouch, the at least one contact patch overlying at least one magnetic contact, the pouch adaptable to be in communication with an electronic member through the at least one contact patch and accept the electronic member within its interior between the first part and the second part of the flexible substrate without disturbing the pouch, the at least one magnetic contact adaptable to slidably align and position the electronic member within the interior of the pouch.

2. The device of claim 1 wherein the pouch is further adaptable to remain affixed to a patient while the electronic member is removed and/or inserted from the interior of the pouch.

3. The device of claim 1 wherein the electronic member comprises a corresponding magnetic contact and the device further comprises the electronic member within the interior of the pouch such that the at least one magnetic contact of the pouch aligns with the corresponding magnetic contact of the electronic member.

4. The device of claim 1 wherein the at least one magnetic contact of the pouch is a ferromagnetic material and the corresponding magnetic contact of the electronic member is a magnet.

5. The device of claim 3 wherein the at least one magnetic contact of the pouch adaptably aligns with the corresponding magnetic contact of the electronic member to cause the contact patch of the pouch overlying the at least one magnetic contact to directly contact a contact located on the electronic member, such that the contact patch of the pouch and the contact located on the electronic member are sandwiched between the at least one magnetic contact of the pouch and the corresponding magnetic contact of the electronic member.

6. The device of claim 1 wherein the device is adaptable to be used with a replaceable electronic member.

7. The device of claim 1 further comprising a ferromagnetic metal adaptable to facilitate a magnetic connection between the pouch and the electronic member.

8. The device of claim 7 wherein the pouch is adaptable to maintain the connection between the electronic member and the pouch.

9. The device of claim 1 further comprising an additional support structure adaptable to maintain the position of the electronics component.

10. The device of claim 1 wherein the at least one magnetic contact is adaptable to provide a low engagement force between the pouch and the electronic member.

11. An electrode device comprising:
a pouch in communication with a patient, said pouch formed from a flexible substrate having a first flexible part and a second flexible part that are inseparably joined together along a periphery, said pouch having an interior, wherein the pouch comprises a conductive trace traversing a distance along the flexible substrate over both the first flexible part and the second flexible part; and
an electronic member adaptable to be slidably inserted and/or removed from the interior of the pouch between the first flexible part and the second flexible part without disturbing the pouch including the joined periphery;
wherein the pouch is adaptable to slidably engage the electronic member and further adaptable to facilitate self-alignment and self-positioning of the electronic member within the interior of the pouch.

12. The device of claim 11 further comprising at least one magnetic contact located on the pouch, the contact adaptable to facilitate the self-alignment and self-positioning of the electronic member.

13. The device of claim 11 wherein the electronic member is adaptable to be slidably inserted, removed, and then reinserted into the interior of the pouch without disturbing the pouch.

14. The device of claim 11 wherein the electronic member is adaptable to be slidably inserted, removed, and replaced with a second electronic member without disturbing the pouch.

15. A method for detecting a physiological parameter with at least one electrode comprising:
positioning a pouch on a surface of a patient, wherein the pouch is formed from a flexible substrate having a first part and a second part that are inseparably joined together along a periphery, the pouch having an interior and comprising a conductive trace traversing a distance along the flexible substrate over both the first part and the second part;
sliding an electronic member into contact with the pouch between the first part and the second part of the flexible substrate to engage the electronic member with the pouch; and
detecting the physiological parameter from the patient.

16. The method of claim 15 wherein the electronics member is adaptable to be inserted and/or removed from the pouch without disturbing the pouch.

17. The method of claim 15 further comprising the step of removing the electronic member from the pouch and replacing the electronic member with a second electronic member.

18. The method of claim 17 wherein the second electronic member is the electronic member.

19. The method of claim 15 wherein the pouch comprises at least one magnetic contact, the pouch adaptable to be in communication with the electronic member, wherein the at least one magnetic contact is adaptable to align and position the electronic member in the pouch.

20. The method of claim 14 wherein the device is adaptable to facilitate insertion of the electronic member in the pouch.

21. A method of detecting a physiological parameter comprising:
forming a pouch from a flexible substrate having a first part and a second part that are inseparably joined together along a periphery, the pouch having an interior and comprising a conductive trace traversing a distance along the flexible substrate over both the first part and the second part, the flexible substrate comprising at least one magnetic contact;
contacting the pouch with a surface of a patient;
inserting an electronic member in the pouch between the first part and the second part of the flexible substrate, the electronic member comprising at least one magnetic contact;
connecting the pouch and electronic member using the at least one magnetic contact on the pouch and the at least one contact on the electronic member; and
detecting at least one physiological parameter from the patient.

22. The method of claim 21 wherein the pouch is further adaptable to remain affixed to a patient while the electronic member is removed and/or inserted from the pouch.

23. The method of claim 21 further comprising the step of disconnecting the electronic member from the pouch and reconnecting the electronic member with the pouch.

24. The method of claim 21 further comprising the step of disconnecting the electronic member from the pouch and reconnecting a new electronic member with the pouch.

25. A method for detecting a physiological parameter from a patient comprising:

sliding an electronic member into contact with a pouch adaptable to be in communication with the electronic member, wherein the pouch is formed from a flexible substrate having a first part and a second part that are inseparably joined together along a periphery, said pouch having an interior and comprising a conductive trace traversing a distance along the flexible substrate over both the first part and the second part and wherein the electronic member is positioned between the first part and the second part of the flexible substrate; and positioning the pouch on a surface of a patient.

26. The method of claim 25 wherein the pouch is further adaptable to remain affixed to a patient while the electronic member is removed and/or inserted from the pouch.

27. The method of claim 25 further comprising the step of removing the electronic member and reinserting the electronic member.

28. The method of claim 25 further comprising the step of removing the electronic member and replacing the electronic member with a second electronic member.

29. A kit for measuring a physiological parameter comprising:

a pouch formed from a flexible substrate having a first part and a second part that are joined together along a periphery, said pouch having an interior and comprising (1) a conductive trace traversing a distance along the flexible substrate over both the first part and the second part and (2) at least one magnetic contact, wherein the pouch is adaptable to be in communication with an electronic member, and wherein the at least one magnetic contact is adaptable to slidably engage the electronics member and is further adaptable to align and position the electronic member in the pouch between the first part and the second part of the flexible substrate.

30. The kit of claim 29 further comprising the electronic member.

31. A kit for measuring a physiological parameter comprising:

a pouch formed from a flexible substrate having a first part and a second part that are inseparably joined together along a periphery, said pouch having an interior and comprising (1) a conductive trace traversing a distance along the flexible substrate over both the first part and the second part and (2) at least one magnetic contact, wherein the pouch adaptable to be in communication with an electronic member; and at least one electronic member adaptable to be inserted and/or removed from the pouch interface without disturbing the pouch, wherein the at least one magnetic contact is adaptable to slidably align and position the electronic member in the pouch between the first part and the second part of the flexible substrate.

32. The kit of claim 31 further comprising more than one electronic member.

33. The device of claim 1 wherein the substrate is a single integral flexible piece, and the first part and the second part are folded together along a hinge and the conductive trace traverses the first part and the second part through the hinge.

34. The device of claim 33 wherein the first part comprises gel contact areas and electrode contact areas configured to contact a patient's skin.

35. The device of claim 33 wherein the second part is at least half the size of the first part.

36. The device of claim 11 wherein the substrate is a single flexible integral piece and the first part and the second part are folded together along a hinge.

37. The device of claim 36 wherein the first part comprises electrode contact areas configured to contact the patient's skin and the second part comprises a second set of contact patches.

38. The device of claim 37 wherein electrode contact areas are electronically connected to the second set of contact patches via one or more traces that traverse the first and second part through the hinge.

39. The device of claim 37 wherein the second part comprises one or more ferromagnetic disks.

40. The device of claim 39 wherein the electronic member comprises a magnet, and the one or more ferromagnetic disks bring the second set of contact patches together with one or more contacts of the electronic member, thereby completing a circuit.

41. The device of claim 11 wherein the first part and the second part are inseparably joined together along the periphery through an adhesive or thermal bonding.

* * * * *

UNITED STATES PATENT AND TRADEMARK OFFICE
CERTIFICATE OF CORRECTION

| | | |
|---|---|---|
| PATENT NO. | : 9,265,435 B2 | Page 1 of 1 |
| APPLICATION NO. | : 12/739553 | |
| DATED | : February 23, 2016 | |
| INVENTOR(S) | : James C. Beck | |

It is certified that error appears in the above-identified patent and that said Letters Patent is hereby corrected as shown below:

In the claims:

Claim 20, column 12, line 36, for the claim reference number "14" should read --15--.

Signed and Sealed this
Seventeenth Day of May, 2016

Michelle K. Lee
*Director of the United States Patent and Trademark Office*